(12) United States Patent
Fartaria De Oliveira et al.

(10) Patent No.: US 11,335,001 B2
(45) Date of Patent: May 17, 2022

(54) METHOD AND SYSTEM FOR MONITORING A BIOLOGICAL PROCESS

(71) Applicants: SIEMENS HEALTHCARE GMBH, Erlangen (DE); CENTRE HOSPITALIER UNIVERSITAIRE VAUDOIS, Lausanne (CH)

(72) Inventors: Mario Joao Fartaria De Oliveira, Saint-Sulpice (CH); Tobias Kober, Lausanne (CH); Benedicte Marechal, Lausanne (CH); Cristina Granziera, Binningen (CH); Meritxell Bach Cuadra, Lausanne (CH)

(73) Assignees: Siemens Healthcare GmbH, Erlangen (DE); Centre Hospitalier Universitaire Vaudois, Lausanne (CH)

( * ) Notice: Subject to any disclaimer, the term of this patent is extended or adjusted under 35 U.S.C. 154(b) by 0 days.

(21) Appl. No.: 16/819,402

(22) Filed: Mar. 16, 2020

(65) Prior Publication Data
US 2020/0294237 A1   Sep. 17, 2020

(30) Foreign Application Priority Data
Mar. 14, 2019   (EP) .................................... 19162761

(51) Int. Cl.
*G06T 7/00* (2017.01)
*G06T 7/38* (2017.01)
(Continued)

(52) U.S. Cl.
CPC .......... *G06T 7/0016* (2013.01); *A61B 5/4842* (2013.01); *G06T 5/009* (2013.01);
(Continued)

(58) Field of Classification Search
CPC . G06T 7/0016; G06T 7/38; G06T 7/11; G06T 7/30; G06T 5/009; G06T 5/50;
(Continued)

(56) References Cited

U.S. PATENT DOCUMENTS

| 5,995,863 | A | * | 11/1999 | Farace | G01R 33/4804 324/307 |
| 2004/0206913 | A1 | * | 10/2004 | Costa | G01N 21/31 250/458.1 |

(Continued)

FOREIGN PATENT DOCUMENTS

| WO | WO-0187155 A1 | * | 11/2001 | ............. A61B 5/055 |
| WO | WO-2017011532 A1 | * | 1/2017 | ............. G06K 9/628 |

OTHER PUBLICATIONS

Bondestam S., Lamminen A., Komu M., Poutanen V. P., Alanen A., and Halavaara J., 1992, Tissue characterization by image processing subtraction: windowing of specific T1 values, Magn. Reson. Imaging 10 989-995. (Year: 1992).*

(Continued)

*Primary Examiner* — Matthew C Bella
*Assistant Examiner* — Kathleen M Broughton
(74) *Attorney, Agent, or Firm* — Laurence A. Greenberg; Werner H. Sterner; Ralph E. Locher

(57) ABSTRACT

A system and a method monitor a biological process. The method includes obtaining an abnormal tissue mask from an abnormal tissue segmentation of an image of an object containing tissue to be analyzed, the image being acquired at a time t0 being a reference time point. Other images of the object are registered onto the abnormal tissue mask, the other images being acquired at other time points. Image contrasts of the other images are normalized with respect to the contrasts of the image acquired at the reference time point. The normalized images are subtracted for each available contrast in order to obtain difference images. A joint (Continued)

difference image is created by summing the previously obtained difference images. A biological process progression map is created by overlapping the abnormal tissue mask obtained and the joint difference image after applying a pre-defined threshold.

9 Claims, 4 Drawing Sheets

(51) Int. Cl.
    *A61B 5/00*     (2006.01)
    *G06T 5/00*     (2006.01)
    *G06T 5/50*     (2006.01)
    *G06T 11/00*     (2006.01)
    *A61B 5/055*     (2006.01)

(52) U.S. Cl.
    CPC ............... *G06T 5/50* (2013.01); *G06T 7/38* (2017.01); *G06T 11/008* (2013.01); *A61B 5/055* (2013.01); *G06T 2207/10081* (2013.01); *G06T 2207/10088* (2013.01); *G06T 2207/10132* (2013.01); *G06T 2207/20224* (2013.01); *G06T 2207/30016* (2013.01); *G06T 2207/30096* (2013.01)

(58) Field of Classification Search
    CPC ......... G06T 11/008; G06T 2207/10081; G06T 2207/10088; G06T 2207/10132; G06T 2207/20224; G06T 2207/30016; G06T 2207/30096; G06T 2207/30004; A61B 5/4842; A61B 5/055; G16H 30/00; G16H 50/20

See application file for complete search history.

(56) References Cited

U.S. PATENT DOCUMENTS

| | | | | |
|---|---|---|---|---|
| 2007/0053560 | A1* | 3/2007 | Miller ................... | G06T 7/0012 382/128 |
| 2010/0220907 | A1* | 9/2010 | Dam ..................... | G06T 7/0012 382/131 |
| 2012/0280686 | A1* | 11/2012 | White .............. | G01R 33/56341 324/309 |
| 2018/0321347 | A1* | 11/2018 | Wang .................... | A61B 5/055 |

OTHER PUBLICATIONS

Fartaria et al.: "Segmentation of Cortical and Subcortical Multiple Sclerosis Lesions Based on Constrained Partial Volume Modeling", in Descoteaux et al. (EDs): MICCAI 2017, Part III, LNCS 10435, pp. 142-149, Springer International Publishing AG, 2017, DOI:10.1007/978-3-319-66179-7-17.

Altay et al.: "Reliability of Classifying Multiple Sclerosis Disease Activity Using Magnetic Resonance Imaging in a Multiple Sclerosis Clinic", JAMA Neurology, vol. 70, No. 3, pp. 338-344, Mar. 2013.

Llado et al.: "Automated detection of multiple sclerosis lesions in serial brain MRI", Neuroadiology (2012), 54, pp. 787-807, DOI 10.1007/s00234-011-0992-6.

Ziga Lesjak et al: "Validation of White-Matter Lesion Change Detection Methods on a Novel Publicly Available MRI Image Database", Neuroinformatics, Humana Press Inc, Boston, vol. 14, No. 4, pp. 403-420, XP036047382, ISSN: 1539-2791, DOI: 10.1007/S12021-016-9301-1 [retrieved on May 20, 2016]; pp. 404-410; 2016.

Ganiler Onur et al: "A subtraction pipeline for automatic detection of new appearing multiple sclerosis lesions in longitudinal studies", Neuroradiology, Springer, DE, vol. 56, No. 5, pp. 363-374, XP035314320, ISSN: 0028-3940, DOI: 10.1007/S00234-014-1343-1; [retrieved on Mar. 4, 2014]; pp. 365; 2014.

Saurabh Jain et al: "Unsupervised Framework for Consistent Longitudinal MS Lesion Segmentation", Image Analysis and Recognition: 11th International Conference, ICIAR 2014, Vilamoura, Portugal, Oct. 22-24, 2014, Proceedings, Part I; In: Lecture Notes in Computer Science, ISSN 1611-3349 ; vol. 8814; [Lecture Notes in Computer Science; Lect.No. XP047419384, ISBN: 978-3-642-17318-9; [retrieved on Jul. 1, 2017]; pp. 210-211; 2017.

Simoes R et al: "Change detection and classification in brain MR images using change vector analysis", Engineering in Medicine and Biology Society, EMBC, 2011 Annual International Conference of the IEEE, IEEE, pp. 7803-7807, XP032320487, DOI: 10.1109/IEMBS.2011.6091923; ISBN: 978-1-4244-4121-1; pp. 7804-7805; 2011.

\* cited by examiner

METHOD AND SYSTEM FOR MONITORING A BIOLOGICAL PROCESS

CROSS-REFERENCE TO RELATED APPLICATION

This application claims the priority, under 35 U.S.C. § 119, of European application EP19162761, filed Mar. 14, 2019; the prior application is herewith incorporated by reference in its entirety.

BACKGROUND OF THE INVENTION

Field of the Invention

The present disclosure is directed, in general, to imaging techniques for imaging biological objects, like tissues, and more specifically to the use of magnetic resonance imaging (MRI) for monitoring a biological process over time.

MRI, computed tomography (CT), ultrasound and other imaging techniques are extensively used for diagnosis and monitoring of various diseases. They offer a wide variety of complementary image contrasts that allow evaluating biological processes related to certain pathologies. Follow-up imaging is often required in order to identify and quantify disease activity and monitor treatment response. The evolution of the pathology can be identified visually comparing scans side-by-side acquired at different time points. However, this manual assessment is tedious, time-consuming and prone to errors, which is reflected in relatively low inter-rater agreement (see for instance Altay et al., Reliability of Classifying Multiple Sclerosis Disease Activity Using Magnetic Resonance Imaging in a Multiple Sclerosis Clinic, JAMA Neurology. 70(3):338-44 (2013)). To address these limitations, several semi-automated or fully-automated approaches have been proposed for time series analyses.

Two main automated techniques exist for time series analyses: a first technique proposes to detect tissue change independently at two time points, wherein longitudinal assessment is computed afterwards through the comparison between two obtained masks segmenting the tissue of interest in both time points, and a second technique proposes a tissue change detection, wherein the differences in consecutive scans are analyzed.

According to the first technique, abnormal tissue masks are determined by segmenting tissue changes separately in each time point. Based on the obtained abnormal tissue masks of each single time point, changes over time are subsequently computed to evaluate a progression of a disease. Misclassification of disease progression can occur due to false negatives in one of the masks or due to under-segmentation or over-segmentation of the abnormal tissue areas, i.e. incomplete segmentation or part of it was not detected. These possible inconsistencies can corrupt the abnormal tissue volume change measurements yielding incorrect evaluation of the disease progression.

According to the second technique, simultaneous analysis of whole image time series, i.e. of all images from all time points, is conducted. Disease progression is evaluated based on the intensity level using e.g. subtraction images of consecutive scans or on the deformation level through deformation fields after applying image registration techniques between consecutive scans. The main problem of this is the number of false positives captured from the subtracted images due to image artefacts and misalignments after registration. These misalignments are more likely to occur at the interface between different tissues. Other problems linked to deformation fields are the lower sensitivity to disease progression due to poor detection of very subtle changes between time points.

BRIEF SUMMARY OF THE INVENTION

An objective of the present invention is to propose a method and a system overcoming the previously mentioned problems, and which notably improves the quantification of a biological process progression and thereby the biological process monitoring by establishing notably an automated and reliable detection of new abnormal tissue.

The objective is achieved according to the present invention by a method and a system for monitoring a biological process according to the object of the independent claims. Dependent claims present further advantages of the invention.

With the foregoing and other objects in view there is provided, in accordance with the invention, a method for monitoring a biological process. The method includes obtaining an abnormal tissue mask from an abnormal tissue segmentation of an image of an object containing tissue to be analyzed, the image being acquired at a time t0 which is a reference time point. Other images of the object are registered onto the abnormal tissue mask, the other images being acquired at other time points. Image contrasts of the other images are normalized with respect to contrasts of the image acquired at the reference time point. Normalized images for each available contrast are subtracted in order to obtain difference images. A joint difference image is created by summing previously obtained difference images. Finally, a biological process progression map is created by overlapping the abnormal tissue mask obtained and the joint difference image after applying a pre-defined threshold.

The present invention proposes to monitor a biological process such as a disease progression, by acquiring two or more images at different points in time and using the information gathered from each time point separately as well as longitudinally between time points (i.e. the difference) for detecting the new abnormal tissue based. Preferentially, contrasts of the acquired images are submitted to a pre-processing pipeline based on registration, intensity inhomogeneity correction, and intensity normalization. Then difference images are obtained by subtracting the normalized images from consecutive time points for each available contrast. If more than one contrast is available, the subtraction images, i.e. the obtained difference images, are summed up in order to obtain a joint difference image. Then, the abnormal tissue mask obtained initially is overlaid on the joint difference image and voxels within the mask with intensity equal or higher to a predetermined threshold on the joint difference image are assigned to a class of biological process, wherein then each class of the voxels is displayed for monitoring a progression/change of the biological process with respect to the time in a map. The map shows therefore the progression of the biological process with respect to the time.

In particular, the present invention proposes to combine the first technique (abnormal tissue mask comparison) and the second technique (i.e. based on difference measurements) in order to yield a more robust approach for evaluation of disease progression. As output, a disease progression map is obtained, where tissue alterations between consecutive scans are indicated. Additionally, this invention uses the complete palette of available contrasts (e.g. different weightings in MRI or images in CT with and without contrast agent) in order to capture complementary information regarding the biological processes. The approach aims at solving the technical issues when the first or the second technique is used alone. Consequently, the number of misclassifications related to the disease progression is reduced.

The foregoing has outlined rather broadly the features and technical advantages of the present disclosure so that those skilled in the art may better understand the detailed description that follows. In particular, the present invention may help a physician to monitor a biological process involving a tissue alteration and/or apparition of abnormal tissue, notably in an organ like a brain.

Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Other features which are considered as characteristic for the invention are set forth in the appended claims.

Although the invention is illustrated and described herein as embodied in a method and a system for monitoring a biological process, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

FIGS. 1 to 5, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

Figure 1:
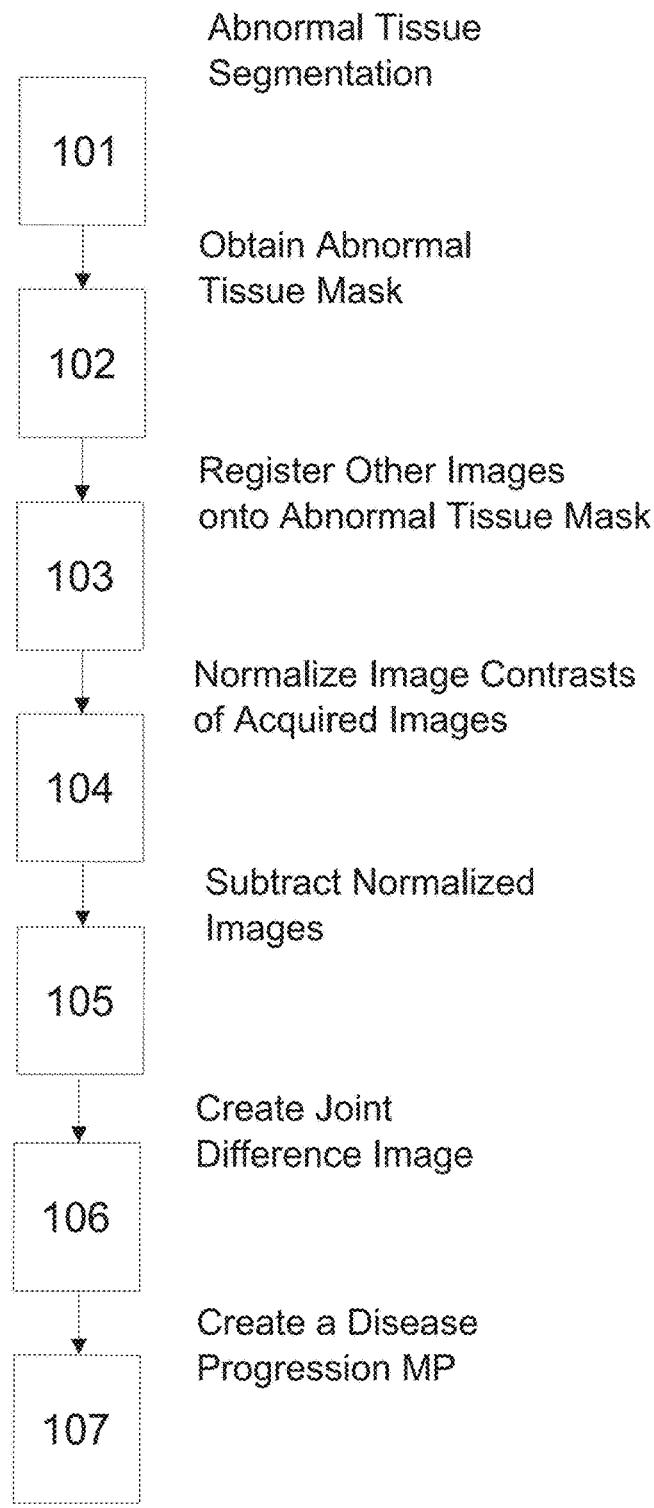
FIG. 1 is a flowchart of a method for monitoring a biological process according to the invention.

Referring now to the figures of the drawings in detail and first, particularly to FIG. 1 thereof, there is shown the different steps of a method 100 for monitoring a biological process and which are carried out by the system according to the invention. The method 100 contains notably the now described steps.

At step 101 and optionally, the system performs an abnormal tissue segmentation from an image of an object comprising tissue to be analyzed, the image being acquired at a time t0 called reference time point by the system or another system not part of the invention. Typically, the reference time point is the most recent date at which the image of the object has been acquired in order to monitor the biological process progression with respect to a current status of the object. Preferentially, an automated tool for abnormal tissue segmentation is used by the system according to the invention to perform the segmentation. A wide number of possible methods to perform abnormal tissue segmentation are known in the art, the methods including both supervised and unsupervised techniques. For instance, the following document provides an overview on lesion segmentation methods in MRI focused on Multiple Sclerosis: Lladó et al., Automated Detection of Multiple Sclerosis Lesions in Serial Brain MRI, Neuroradiology 54(8):787-807 (2012)).

At step 102, the system obtains an abnormal tissue mask from the abnormal tissue segmentation performed for the image characterizing the object at the reference time point. The mask might be extracted by the system from the previously obtained abnormal tissue segmentation, or, if step 101 is not performed by the system according to the invention, then the mask might be received by the system from a tool or device configured for carrying out step 101.

At step 103, the system registers other images of the object onto the abnormal tissue mask, so that the other images and the abnormal tissue mask are aligned with each other with respect notably to the reference time point, wherein the other images have been acquired at other time points, which are preferentially previous time points. In particular, the other images are rigidly registered onto the abnormal tissue mask. According to the registration process, the other images acquired at other time points are aligned in space with the abnormal tissue mask obtained from an image of the object at time t0, making it possible therefore to overlap common features and highlight differences. Additionally, another image acquired at the reference time point might be registered onto the abnormal tissue mask for obtaining another contrast information.

At step 104, the system normalizes image contrasts of the images acquired at the other time points with respect to contrasts of the image acquired at the reference time point. By this way, contrast intensity inhomogeneities in each one of the other images might be corrected. Preferably, the system iteratively processes each of the other images, wherein for each contrast, contrast intensities of a previous time point image are normalized to the contrast intensities of the image or images acquired at the reference time point using an appropriate method (e.g. histogram matching).

At step 105, the system subtracts normalized images for each available contrast in order to obtain difference images, wherein the subtraction is made for normalized images that come from images acquired at consecutive time points, wherein the image acquired at the reference time point is considered as the normalized image at the reference time point. In case the abnormal tissue is shown as hyperintense signal, the image acquired at the reference time point is considered as the first term of a subtraction equation configured for calculating said difference images. In case the abnormal tissue is shown as hypointense signal, the image acquired at the reference time point is considered as the second term of the subtraction equation. Preferentially, all the obtained difference images are scaled between 0 and 1.

At step 106, the system creates a joint difference image by summing the previously obtained difference images.

At step 107, the system creates a biological process (e.g. a disease) progression map by overlapping the abnormal tissue mask obtained at step 102 and the joint difference image obtained at step 106 after applying a predefined threshold. In particular, tissue voxels within the mask with intensity equal or higher to the predefined threshold on the joint difference image are considered as representing an abnormal change in the tissue and are assigned to a class of a biological process, e.g. to a "disease progression". The biological process progression map is obtained by grouping all the voxels that are assigned to a same class of a biological process in an image of the object.

By combining the first technique and the second technique, a more reliable biological process progression map can be obtained. Advantageously, the method according to the invention constrains the evaluation of abnormal tissue progression in the subtracted image to regions where abnormal tissue is present rather than to the whole object (e.g. organ) of interest. This decreases the chance of misclassifications in challenging areas due to registration errors or image artefacts. The method according to the invention also reduces misclassifications due to under- or over-segmentation of abnormal tissue when volume changes between two time points are computed by comparing abnormal tissue masks as required by prior art techniques. In addition, information from more than one available contrast can be used by combining the respective difference images (defined here as joint difference image). The joint difference image captures the complementary tissue alterations in consecutive time points, and is less prone to artefacts or misalignment effects compared to a single difference image.

Figure 2:
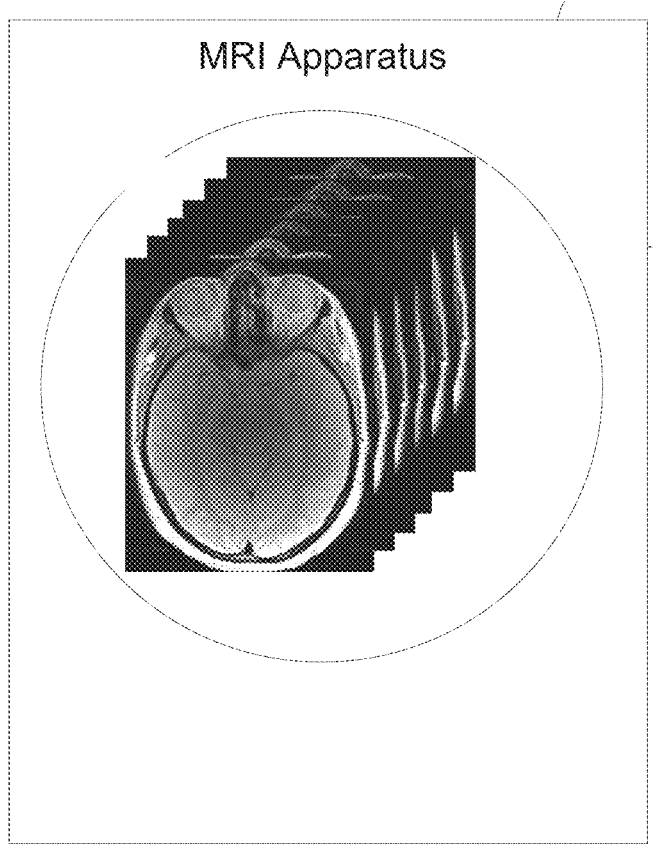
FIG. 2 is an illustration of a system for implementing the claimed method.

FIG. 2 illustrates a system 200 for monitoring a biological process by automatically creating a progression map of the biological process. The system contains:
a) optionally, a magnetic resonance imaging (MRI) apparatus 201 configured for acquiring images for an object, e.g. brain images of a subject, in order to enable tissue analysis;
b) a database 202 or memory for storing data required for creating the progression map;
c) a processing unit 203 configured for processing said data required for creating the progression map, the processing unit 203 containing notably an abnormal tissue segmentation tool;
d) a display 204 for displaying the progression map; and
e) wherein the system 200 according to the invention is configured for performing the steps of the method for creating and then displaying the progression map.

Figure 3:
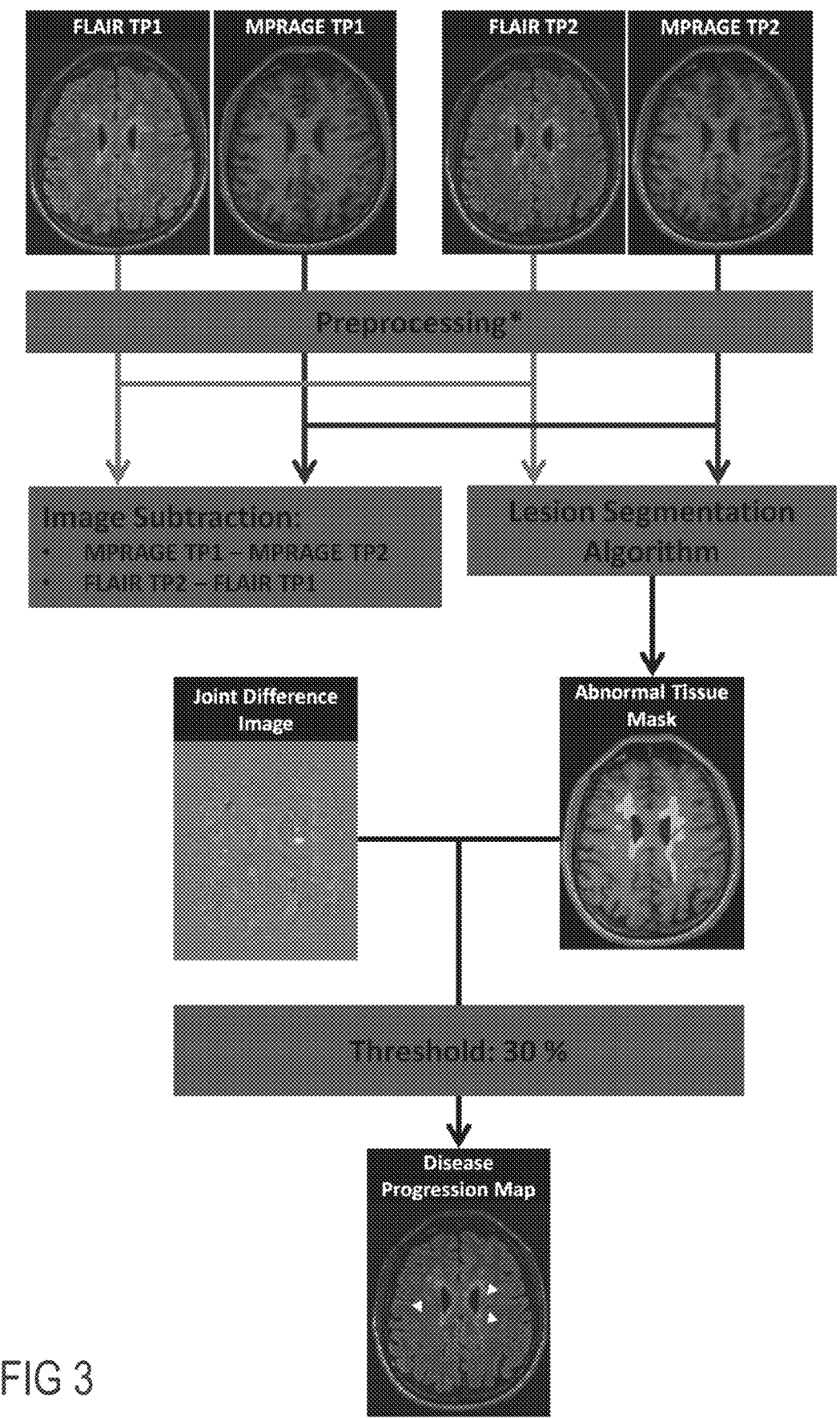
FIG. 3 is an illustration of a creation of a disease progression map according to the claimed method.

FIG. 3 shows a conceptual overview of the method according to the invention. In this case, the method is used to obtain the disease progression map of follow-up in multiple sclerosis (MS) lesions (considered as abnormal tissue in this case). The MRI complete palette of available image contrasts in this specific case is composed by T1 MPRAGE and T2 FLAIR contrasts from two time points (time point 1—hereafter TP1, and time point 2—hereafter TP2). All the images undergo a pre-processing step based on registration to MPRAGE TP2, N4 bias field correction and histogram matching for intensity normalization. Preferentially, the segmentation algorithm proposed by Fartaria et al. (Segmentation of Cortical and Subcortical Multiple Sclerosis Lesions Based on Constrained Partial Volume Modeling, in Descoteaux et al. (Eds), MICCAI 2017, Part III, LNCS 10435, pp. 142-149, Springer International Publishing) is used to obtain a lesion mask from images acquired at the reference time point. Two difference images are obtained for the MPRAGE and FLAIR, respectively. As lesions appear as hypointense signal in MPRAGE, the subtraction is performed considering the TP1 as the first term as presented in the following equation: MPRAGE TP1−MPRAGE TP2. The difference image from FLAIR is obtained considering the TP2 as the first term of the equation because lesions appear as hyperintense signal: FLAIR TP2−FLAIR TP1. FLAIR and MPRAGE difference images are combined in a joint difference image. Voxels assigned to lesion class in the lesion mask with intensity equal or higher than 30% in the joint difference image are assigned to the disease progression class. Finally, all the voxels identified as part of disease progression are shown in a binary map as disease progression map. In this particular case, the disease progression map corresponds to areas of new and enlarged lesions in a MS patient.

Figure 4:
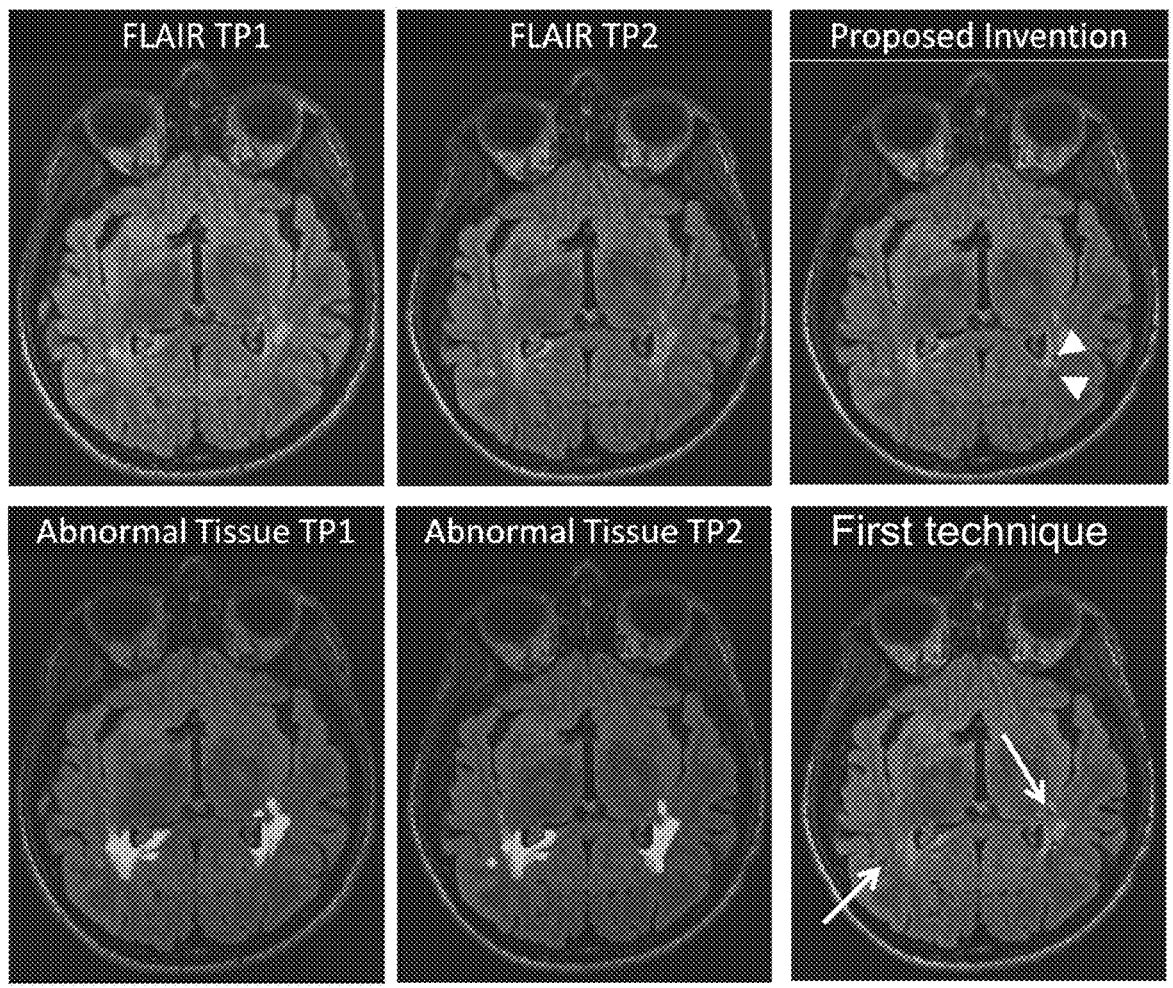
FIGS. 4 and 5 are illustrations of the advantages of the present invention in front of the first and second techniques.
Figure 5:
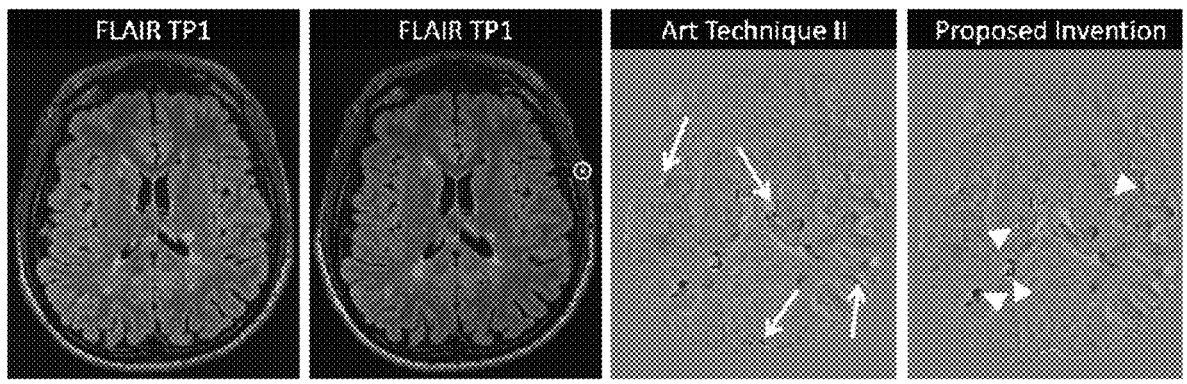

Advantages of the proposed method with respect to the first and second techniques are shown in FIG. 4 and FIG. 5, respectively. FIG. 4 shows FLAIR images of axial slices of a brain acquired at different time points, the respective lesion masks, and the results of disease progression from the proposed method and from the first technique. False positives in the disease progression map (see white arrows) appeared due to under- or over-segmentation of lesions in one of the time points. FIG. 5 shows FLAIR images of axial slices of a brain acquired at different time points, and the results of disease progression, overlaid in the combined difference map, from the second technique and from the proposed method. False positives observed in the disease progression map (see white arrows) are mainly due to registration misalignments. Such false positives are not observed in images obtained according to the present invention.

In summary, the proposed technique takes the advantages of the first and second techniques, reducing the number of misclassifications yielding a more reliable disease progression evaluation.

The invention claimed is:
1. A method for monitoring a biological process, which comprises:
obtaining, by a magnetic resonance imaging apparatus, an abnormal tissue mask from an abnormal tissue segmentation of an image of an object including tissue to be analyzed, the image being acquired at a time t0 which is a reference time point, wherein the magnetic resonance imaging apparatus includes a palette of available image contrasts;
registering other images of the object onto the abnormal tissue mask, the other images being acquired at other time points, wherein for each of said other time points, at least two images are acquired, each for a different contrast of the palette of available contrasts;
for each of the different contrasts for which the other images have been acquired, normalizing image contrasts of the other images with respect to contrasts of the image acquired at the reference time point;
subtracting normalized images for each available contrast in order to obtain difference images;
creating a joint difference image by summing the difference images the summing being a combination of the difference images obtained for the respective different contrasts; and
creating a biological process progression map by overlapping the abnormal tissue mask obtained and the joint difference image after applying a pre-defined threshold.
2. The method according to claim 1, which further comprises performing the abnormal tissue segmentation from the image of the object.

3. The method according to claim 1, wherein the normalizing step further comprises iteratively processing each one of the other images, wherein for each contrast, contrast intensities of a previous time point image are normalized to contrast intensities of the image acquired at the reference time point using an appropriate method.

4. The method according to claim 1, wherein a subtraction is performed for the normalized images that come from images acquired at consecutive time points, and wherein the image acquired at the reference time point is considered as the normalized image at the reference time point.

5. The method according to claim 1, wherein in a case where the abnormal tissue is shown as a hyperintense signal, then the image acquired at the reference time point is considered as a first term of a subtraction for calculating the difference images, and in a case where the abnormal tissue is shown as a hypointense signal, then the image acquired at the reference time point is considered as a second term of the subtraction.

6. The method according to claim 1, wherein all the difference images obtained are scaled between 0 and 1.

7. The method according to claim 1, wherein tissue voxels within the abnormal tissue mask with an intensity equal or higher to a predefined threshold on the joint difference image are considered as representing an abnormal change in the tissue and are assigned to a class of the biological process.

8. The method according to claim 7, which further comprises grouping all the tissue voxels that are assigned to a same class of the biological process in the image of the object.

9. A system for monitoring a biological process, the system comprising:
   a magnetic resonance imaging apparatus configured for acquiring images of an object in order to enable object tissue analysis;
   a memory for storing data required for creating a progression map;
   a processor configured for processing the data required for creating the progression map, said processor having notably an abnormal tissue segmentation tool;
   a display for displaying the progression map;
   wherein the system is configured for performing a method for monitoring the biological process, the system programmed to:
      obtain, by said magnetic resonance imaging apparatus, an abnormal tissue mask from the abnormal tissue segmentation of the image of the object including tissue to be analyzed, the image being acquired at a time t0 which is a reference time point, wherein said magnetic resonance imaging apparatus includes a palette of available image contrasts;
      register other images of the object onto the abnormal tissue mask, the other images being acquired at other time points, wherein for each of said other time points, at least two images are acquired, each for a different contrast of the palette of available contrasts;
      for each of the different contrasts for which the other images have been acquired, normalize image contrasts of the other images with respect to contrasts of the image acquired at the reference time point;
      subtract normalized images for each available contrast in order to obtain difference images;
      create a joint difference image by summing the difference images, the summing being a combination of the difference images obtained for the respective different contrasts; and
      create the progression map by overlapping the abnormal tissue mask obtained and the joint difference image after applying a pre-defined threshold.

* * * * *